US007470257B2

(12) United States Patent
Norton et al.

(10) Patent No.: US 7,470,257 B2
(45) Date of Patent: Dec. 30, 2008

(54) SYRINGE SAFETY DEVICE

(75) Inventors: Paul H. Norton, Trumbauersville, PA (US); John R. Wolfe, Selinsgrove, PA (US)

(73) Assignee: West Pharmaceutical Services, Inc., Lionville, PA (US)

( * ) Notice: Subject to any disclaimer, the term of this patent is extended or adjusted under 35 U.S.C. 154(b) by 348 days.

(21) Appl. No.: 10/727,868

(22) Filed: Dec. 4, 2003

(65) Prior Publication Data

US 2004/0112457 A1 Jun. 17, 2004

Related U.S. Application Data

(63) Continuation of application No. 10/011,262, filed on Nov. 7, 2001, now Pat. No. 6,729,370.

(60) Provisional application No. 60/246,635, filed on Nov. 8, 2000.

(51) Int. Cl.
*A61M 5/00* (2006.01)

(52) U.S. Cl. ........................ 604/187; 604/181; 604/414

(58) Field of Classification Search .................. 604/82, 604/87, 88, 187, 411, 414, 181, 415
See application file for complete search history.

(56) References Cited

U.S. PATENT DOCUMENTS

| | | | |
|---|---|---|---|
| 2,326,490 | A | 8/1943 | Perelson |
| 3,826,260 | A | 7/1974 | Killinger |
| 3,938,518 | A | 2/1976 | Tischlinger |
| 4,439,184 | A | 3/1984 | Wheeler |
| 4,516,967 | A | 5/1985 | Kopfer |
| 4,568,346 | A | 2/1986 | Van Dijk |
| 4,619,651 | A | 10/1986 | Kopfer et al. |
| 4,768,568 | A | 9/1988 | Fournier et al. |
| 4,932,939 | A | 6/1990 | Magre et al. |
| 5,088,996 | A | 2/1992 | Kopfer et al. |
| 5,125,908 | A | 6/1992 | Cohen |
| 5,171,220 | A | 12/1992 | Morimoto |
| 5,222,945 | A | 6/1993 | Basnight |
| 5,247,972 | A | 9/1993 | Tetreault |
| 5,520,659 | A | 5/1996 | Hedges |
| 5,584,808 | A | 12/1996 | Healy |
| 5,605,542 | A | 2/1997 | Tanaka et al. |

(Continued)

FOREIGN PATENT DOCUMENTS

| | | |
|---|---|---|
| EP | 0 417 988 A1 | 3/1991 |
| FR | 2 717 086 A1 | 9/1995 |
| GB | 2 235 135 A | 2/1991 |
| JP | 10033675 | 2/1998 |
| WO | WO 00/54723 A1 | 9/2000 |

*Primary Examiner*—Kevin C Sirmons
*Assistant Examiner*—Phillip Gray
(74) *Attorney, Agent, or Firm*—Panitch Schwarze Belisario & Nadel LLP

(57) ABSTRACT

A syringe safety device coupling between a vial and a syringe, including a tubular connector having a first axial end receiving the vial and a second, opposing axial end releasably receiving a syringe. The tubular connector encloses a sliding joint having opposing open axial ends and a passageway between the ends. A first sliding joint end is adapted to engage a syringe needle. A second sliding joint end is configured to releasably engage a needle receiver. The syringe is releasably removable from the sliding joint after fluid coupling with the vial through the sliding joint, without removal of the needle or the sliding joint from the connector, which captures the needle with the sliding joint in the connector. The first end of a joint includes a receiver, adapted to releasably receive a removable syringe needle, and a mount, adapted to releasably receive a releasable needle receiver of a syringe.

14 Claims, 5 Drawing Sheets

U.S. PATENT DOCUMENTS

| | | | | | |
|---|---|---|---|---|---|
| 5,653,698 | A | | 8/1997 | Niedospial et al. | |
| 5,685,846 | A | | 11/1997 | Michaels, Jr. | |
| 5,827,262 | A | * | 10/1998 | Neftel et al. | 604/414 |
| 5,899,881 | A | | 5/1999 | Grimard et al. | |
| 5,971,953 | A | | 10/1999 | Bachynsky | |
| 6,019,750 | A | | 2/2000 | Fowles et al. | |
| 6,149,623 | A | | 11/2000 | Reynolds | |
| 6,253,804 | B1 | | 7/2001 | Safabash | |

* cited by examiner

SYRINGE SAFETY DEVICE

CROSS-REFERENCE TO RELATED APPLICATIONS

This patent application is a continuation of U.S. patent application Ser. No. 10/011,262, filed Nov. 7, 2001 now U.S. Pat. No. 6,729,370, which claims priority to U.S. Provisional Patent Application No. 60/246,635, filed Nov. 8, 2000, entitled "Syringe Safety Device," the subject matter of which is incorporated herein by reference.

BACKGROUND OF THE INVENTION

This invention is directed to a syringe safety device and, more specifically, to a syringe device that allows a user to reconstitute medicine in sealed vials without risk of the user being stuck by a needle needed to access the contents of the vial. It is often desirable to store drugs in a concentrated or powdered (e.g., lyophilized) form until just prior to administering the drug to a patient at which time the medicine is mixed with a solvent of diluent or rehydrant. Several different arrangements for mixing such drugs and liquids have been disclosed.

U.S. Pat. No. 5,653,698 discloses a safety coupling system for reconstituting medications that employ a special tubular coupling (10) having a hub (20) containing a shielded needle cannula (12). The coupling system (10) can be joined with a special syringe that receives a special medication containing cartridge (40). The opposing end of the hub can be provided with Luer threads or can be designed to mate with an adapter in the form of a "pre-slit injection site" (72), which is threaded to be mounted on a tubular receiver. The requirement for use with a special cartridge containing syringe limits its broad utility. Also, the cannula, which has a smooth uniform outside diameter must be absolutely secured against sliding movement with respect to the hub or the cannula will be pushed from the hub when the syringe is pressed into its fluid coupling position in the proximal end (22) of the first sleeve (30) of the hub (20).

U.S. Pat. No. 5,827,262 discloses another device for coupling together a conventional syringe and a medicament containing vial. A number of embodiments are disclosed but vary only slightly in detail. Each embodiment includes a tubular guide (e.g., 14) designed to receive a conventional vial at one end and a conventional syringe at the opposing end. The tubular guide (14) directs the needle (34) of a conventional syringe (12) into contact with of the stopper (22) of the vial (10) by providing a tubular slide member (48) which receives a distal end of the syringe and slidingly supports the distal end of the syringe as the needle of the syringe passes through a penetrable barrier (40) or small diameter opening in the center of the guide tube. Some embodiments are designed to release the syringe with its needle after a medicament has been drawn into the syringe from the vial. An alternative embodiment provides for the needle to detach from the end of the syringe during withdrawal of the syringe, leaving the needle implanted in the stopper or in the penetrable barrier.

U.S. Pat. No. 6,019,750 discloses a tubular connector device (10) that is designed to fluidly couple a conventional medicinal vial with piercable stopper and a flexible solution container or bag of the type having an injection port in the form of a separate tube extending from the bag and having its end sealed with a piercable stopper or other penetrable septum. The device (10) has first and second sleeves or tubes (30, 32), which are telescopically coupled together and which contain a double ended piercing member (34) or cannula. The device (10) further includes a foil (58) and a sealing member (103) in the two sleeves (32, 34) to seal the cannula (34) within the extended sleeves before use. In use, the sleeves (30, 32) are compressed together. One pointed end of the cannula within the second sleeve (32) is moved to the distal end of the sleeve in a position where it can pierce the stopper of a vial. The distal end of the first sleeve (30) has an annular gap between the sidewall of the sleeve and the cannula (34) to receive the tubular port (20) of the flexible bag (12) and to pierce the septum (22) located in the distal end of that port (20). The distal end (82) of the second tube (32) has an enlarged cavity (86) with plural spring fingers (84*a*) to secure the end of a vial (14) so that the vial could not normally be removed once attached without visible damage to the fingers (84*a*). The device also includes locking elements (50, 144, 146) to prevent the sleeves from being re-extended once they are compressed into the activated state. The same means prevent relative rotational movement of the sleeves with respect to one another in the activated state.

The U.S. Pat. No. 6,019,750 connector is designed to attach a medicinal vial (14) to a flexible fluid bag (12) for dilution and requires that once the vial is attached to the bag and in communication with the fluid in the bag, the bag must be squeezed to deliver fluid to the interior of the vial. Then the bag, the connector and the vial all shaken together to mix the original vial contents with the added liquid in the bag. The bag is then again manipulated and re-squeezed to force compressed air into the vial so that when the bag is released from compression and the vial held upside down over the bag, its fluid contents will leak through the cannula into the bag. All three devices should again be shaken to fully mix the reconstituted medication with the remaining fluid in the bag. Such a mode of operation is not always convenient. If the caregiver has time to attach the connector and vial to the fluid bag before the bag is connected to the patient, such manipulation and agitation can take place away from the patient without disturbing the patient. However, that is not always possible. The drug may have to be given to the patent while the patient is already connected with the bag. Agitation of the bag and vial at that can be disturbing to the patient and can sometimes result in separation of the catheter tube from the needle connecting the bag to the patient or of the catheter needle from the patient.

It would be desirable to provide a similar safety device which permits mixing of hazardous ingredients in a stoppered vial with the contents of a fluid bag without exposing the user to the possibility of a needle stick and yet minimizes the manipulation of the bag.

SUMMARY OF THE INVENTION

A syringe safety device configured to form a fluid coupling between a sealed vial and a syringe, the syringe safety device comprising: a tubular connector having opposing first and second axial open ends, the first open axial end being adapted to engage an end of a conventional medicine vial with stopper; and a sliding joint received in the second open axial end of the tubular connector, the sliding joint having opposing first and second axial ends and a passageway between the first and second axial open ends, the first axial open end being adapted to engage with an enlarged, blunt mounting end of a syringe needle, the second axial end of the sliding joint further being adapted to releasably engage at least a releasable needle receiver on a distal end of a barrel of a conventional syringe without needle, the syringe being releasably removable from the sliding joint after fluid coupling with the vial through the passageway of the sliding joint without removal of the sliding joint from the tubular connector and without the needle.

BRIEF DESCRIPTION OF THE SEVERAL VIEWS OF THE DRAWINGS

The following detailed description of the preferred embodiment of the invention will be better understood when read in conjunction with the appended drawings. For the purpose of illustrating the invention, there is shown in the drawings an embodiment which is presently preferred. It is understood, however, that the invention is not limited to the precise arrangement and instrumentality shown. In the drawings.

DETAILED DESCRIPTION OF THE INVENTION

Figure 1:
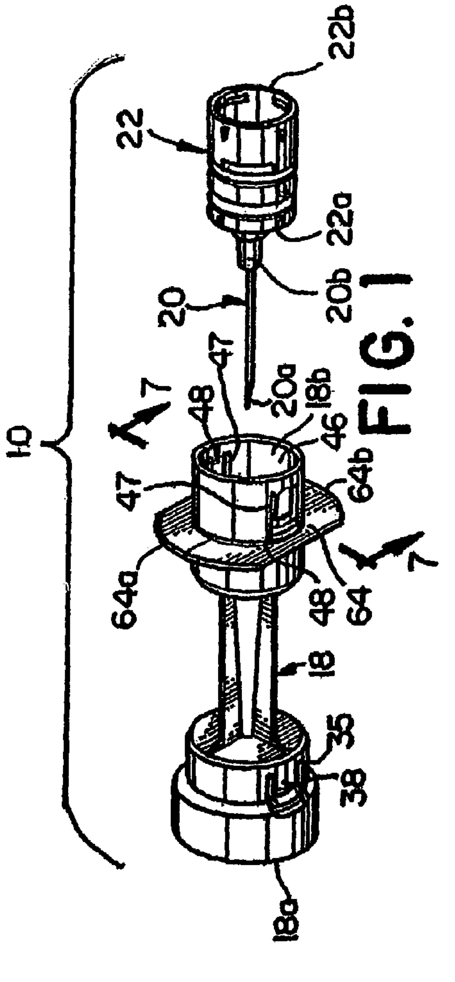
FIG. 1 is a perspective, partially exploded view of a syringe safety device of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the syringe safety device and designated parts thereof. The terminology includes the words above specifically mentioned, derivatives thereof, and words of similar import.

Figure 2:
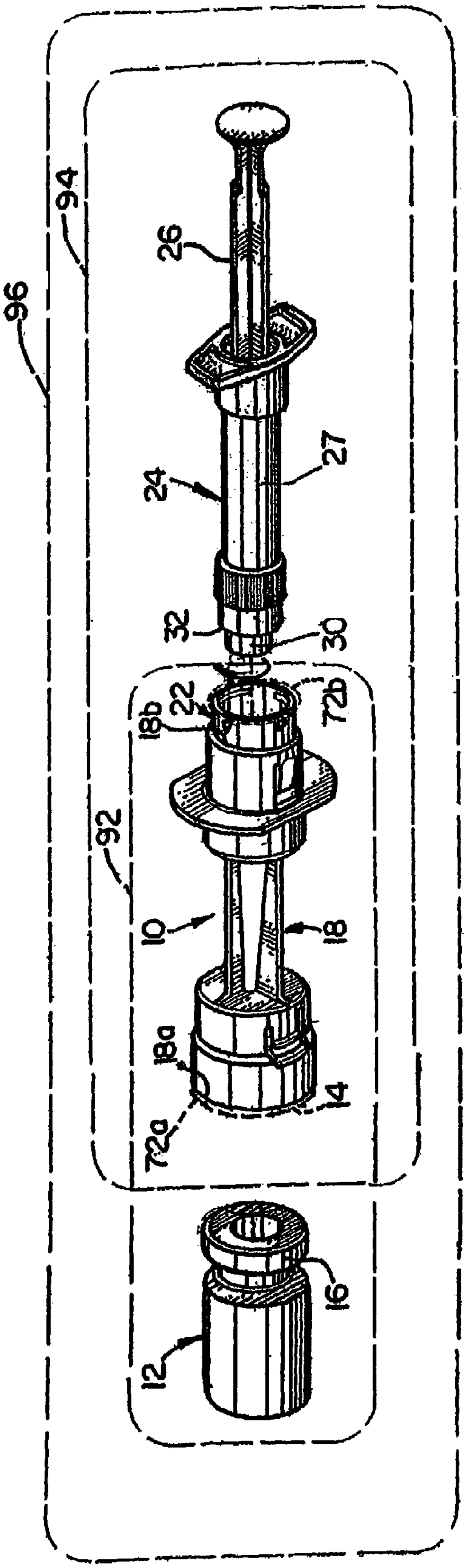
FIG. 2 is a perspective view of the device of FIG. 1 in an assembled state before use.
Figure 3:
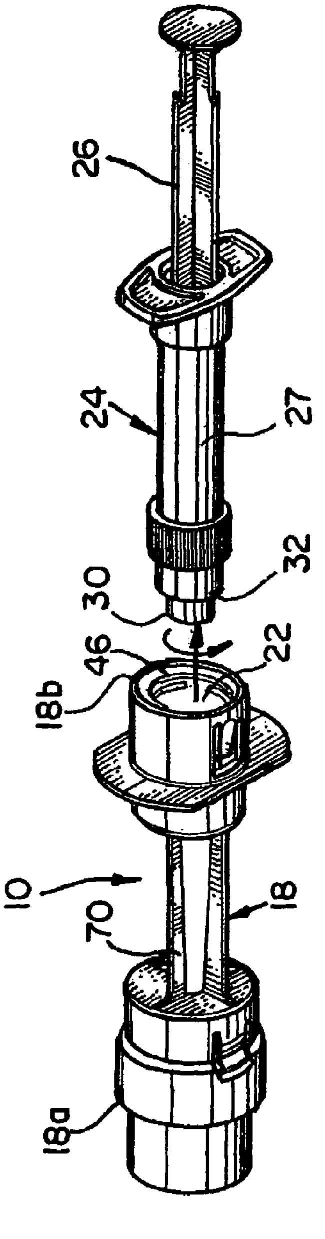
FIG. 3 is a perspective of the assembly after use with the syringe removed.

Referring to the drawings in detail wherein like numerals represent like elements throughout, FIGS. 1-6 illustrate a syringe safety device according to the present invention, generally designated at 10. Briefly stated, the syringe safety device 10 of the present invention allows a user to reconstitute medicine, or withdraw fluid from a stoppered vial 12, without exposing the user to any potential needle sticks. The syringe safety device 10 allows a user to inject the contents of a syringe 24 without needle into a vial 12 for mixture with another material contained in the vial. Once the contents of the vial 12 are mixed and ready for use, a plunger rod 26 is partially withdrawn from the barrel 27 of the syringe 24 causing the contents of the vial 12 to be drawn through the device 10 into the syringe 24. The syringe 24 containing the desired amount of mixed medication can be disengaged from the syringe safety device 10 without removing a needle 20 from the syringe safety device 10 (FIG. 3). Then, a needle receiver 30 on a distal end 32 of the syringe 24 can be attached to a mating part on a catheter or other tube or on an intravenous bottle or bag or the like (none shown) to transfer the contents of the syringe 24 into a patient. During the entire use of the syringe safety device 10, the user is not exposed to the needle 20 it contains.

Figure 4:
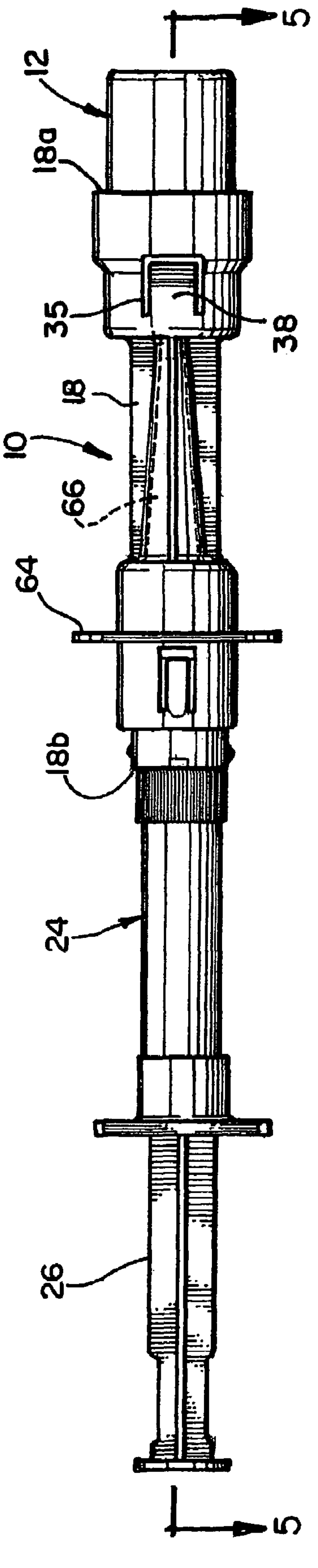
FIG. 4 is a side elevation view of the syringe safety device of FIG. 2 coupled with and between a conventional medicine vial with stopper and a conventional syringe with removable needle removed.
Figure 5:
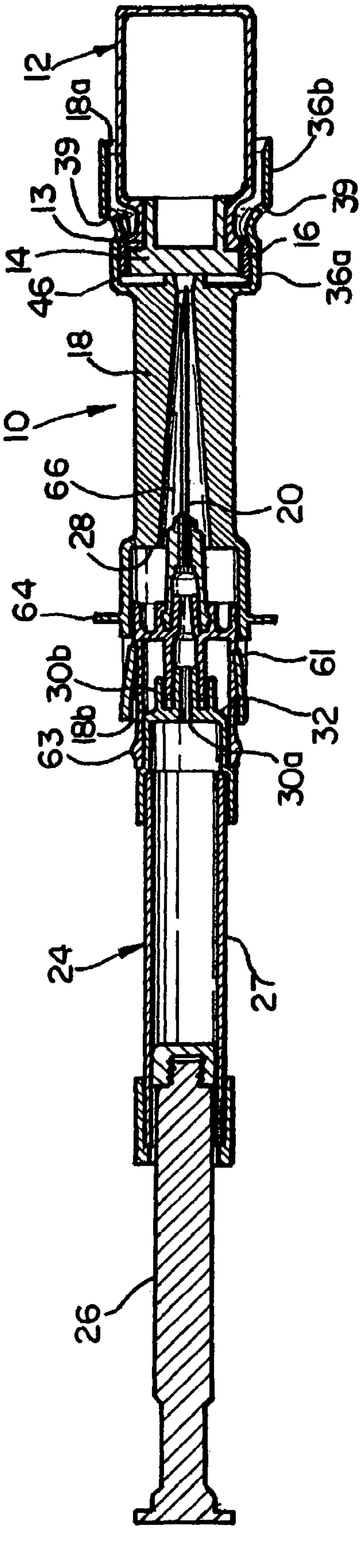
FIG. 5 is an axial cross-sectional view taken along lines 5-5 in FIG. 4 before use.
Figure 6:
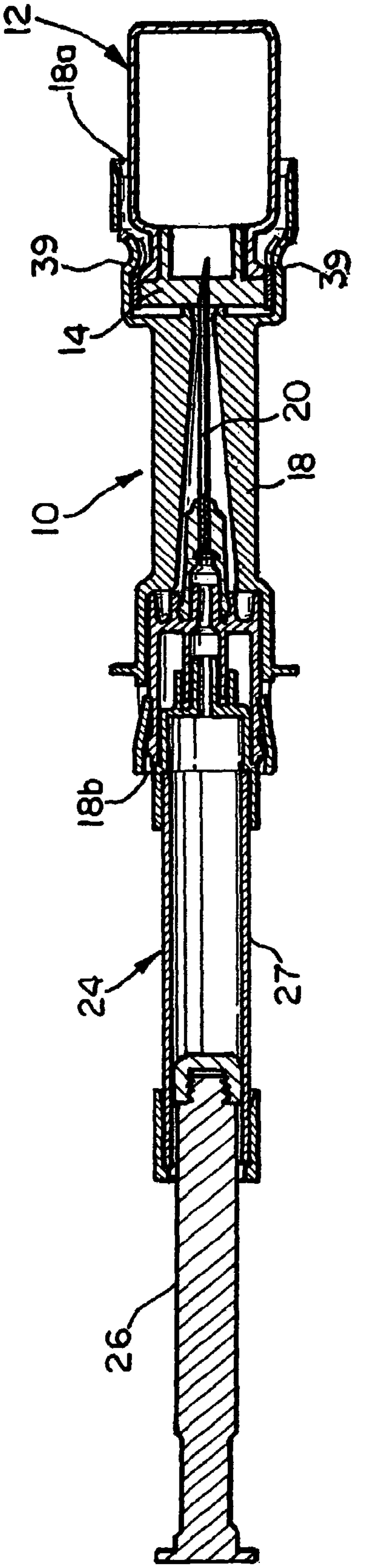
FIG. 6 is an axial cross-sectional view of the assembly of FIGS. 4-5 during use.

The syringe safety device 10 is shown in the various FIGS. 1-6 and is primarily formed by a preferably, but not necessarily, generally cylindrically shaped generally tubular connector 18 having first and second opposing open ends 18*a*, 18*b*. A first open end 18*a* of the connector 18 is preferably configured to attach to a sealed vial 12 (FIGS. 3-6). An opposing, second open end 18*b* of the connector 18 is preferably configured to releasably receive the syringe without needle 24 (FIGS. 4-6). The connector 18 is preferably formed from durable, high strength material, such as polycarbonate or the like. An elongated circumferential flange 64 defines a pair of radially outwardly projecting finger grips 64*a*, 64*b* but a circular circumferential flange or a pair of opposed individual flanges or a separate member (none depicted) on the connector 18 or the like can be provided to assist in using the connector 18 as will be subsequently explained.

Figure 7:
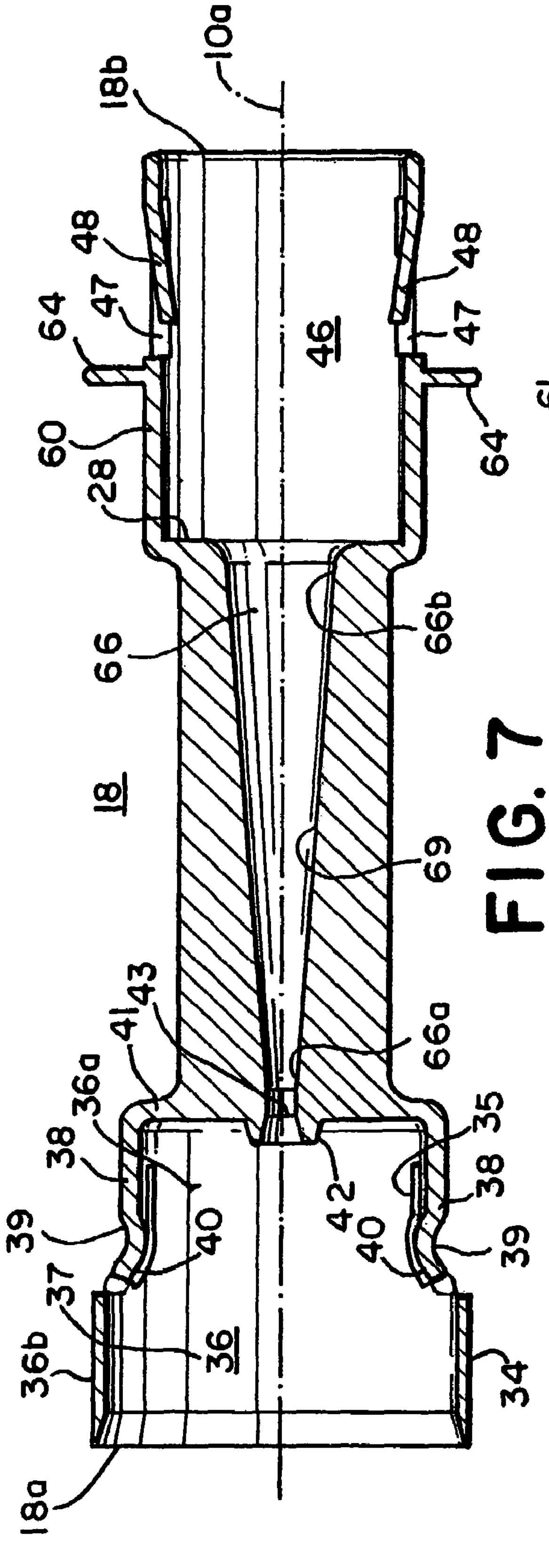
FIG. 7 is an axial cross section of the tubular connector of the device taken along the lines 7-7 in FIG. 1.
Figure 12:
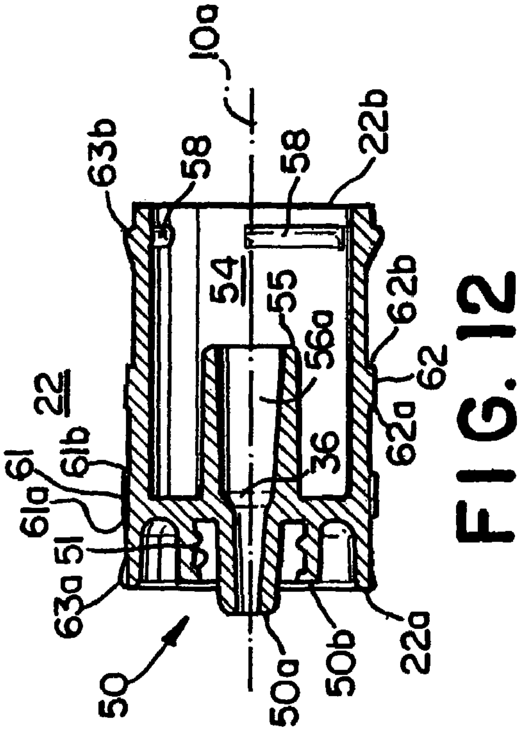
FIG. 12 is an axial cross-sectional view taken along the lines 12-12 in FIG. 10 of the sliding joint of the device.

More particularly, referring to FIG. 7, the first and second opposing open ends 18*a*, 18*b*, respectively of the connector 18, have respective first and second open ended cavities 36 and 46, respectively. The open ended cavities 36, 46 are aligned and in fluid connection and communication with one another, preferably through a central passageway indicated generally at 66, along an axis 10*a*, which is a central longitudinal axis of the device 10 and each of its components including connector 18. The first open cavity 36 is sized and shaped to receive a stopper end 14*a* of the vial 12 as best seen in FIGS. 4-6. The connector 18 further including at least one and, preferably a plurality of integral, spring clip members or "fingers" 38 and 48 located proximal the first end 18*a* and second end 18*b*, respectively, which are configured to secure the stopper end of the vial 12 in the first cavity 36 and non-releasably retain the remaining components of the device 10 in the connector 18.

Figure 8:
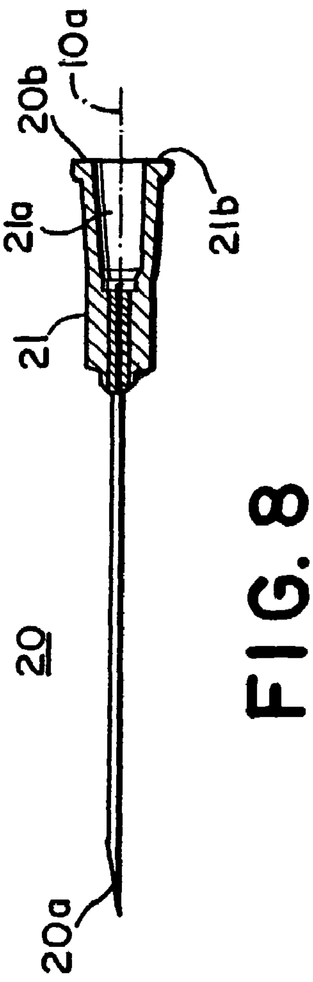
FIG. 8 is an axial cross-sectional view of the needle of the device.
Figure 9:
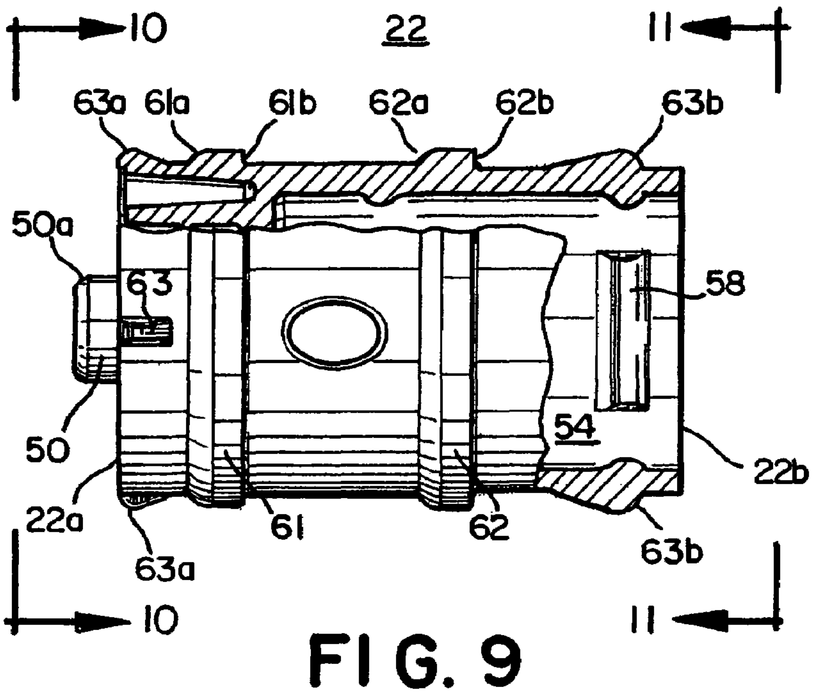
FIG. 9 is a partially broken away side elevation of the sliding joint.
Figure 10:
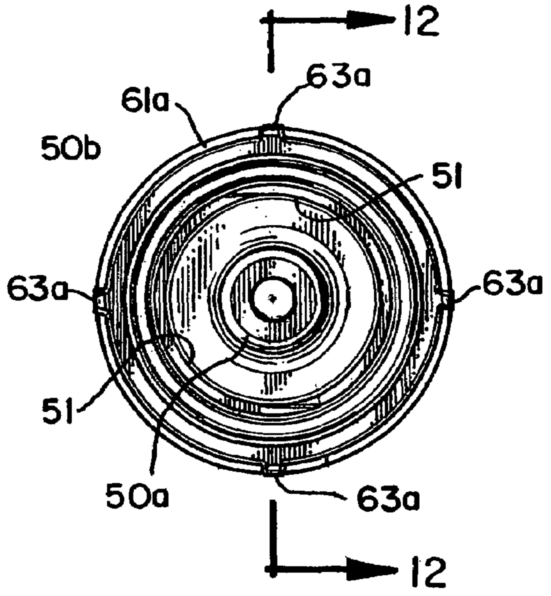
FIG. 10 is an end view from lines 10-10 in FIG. 9.
Figure 11:
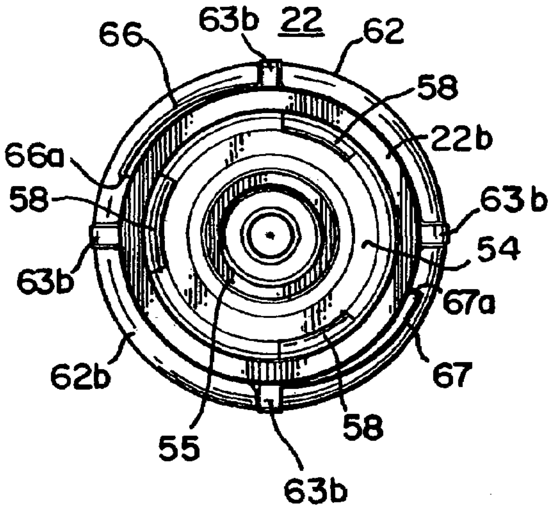
FIG. 11 is an end view from lines 11-11 in FIG. 9.

The remaining components of the device 10 include a cannula, preferably in the form of a conventional, removable syringe needle 20, and a sliding joint 22. The needle 20 and sliding joint 22 are shown assembled in FIG. 1 and assembled with the tubular connector 18 in FIGS. 2-6. They are shown individually in FIGS. 8 and 9-12, respectively. When device 10 is assembled, the needle 20 is generally axially oriented in the connector 18, in the central passageway 66 and the second cavity 46. Referring to FIG. 8, the needle 20 has opposing longitudinal ends, a first pointed end 20*a* which faces the first end 18*a* of the connector 18 when the device 10 is assembled, and a second, enlarged blunt mounting end 20*b*. Suggestedly, the needle 20 is a conventional, syringe needle designed for removable mounting by threads, friction, lugs, etc. to a conventional syringe. Preferably, the blunt mounting end of the needle 20 has a Luer connector in the form of the bell shaped mating member 21 with a generally tapered inner bore 21*a* and radially outwardly flared circumferential flange 21*b* of a removable syringe needle capable of releasably mating with either a conventional Luer lock type needle receiver or a conventional Luer slip type needle receiver.

As best seen in FIGS. 9-12, the sliding joint 22 has first and second opposing axial ends 22*a* and 22*b*, respectively. When assembled with the needle 20, the first axial end 22*a* is engaged preferably releasably engaged with the enlarged blunt mounting end 20*b* of the needle 20 (see FIGS. 1 and 4-6) to move the needle 20 with the sliding joint 22 in the second cavity 46 and in the passageway 66 into the first cavity 36 (FIG. 6). The sliding joint 22 is configured to form a leak resistant fluid coupling between the enlarged blunt mounting end 20*b* of the needle 20 and the sliding joint 22. Preferably, the first axial end 22*a* of the sliding joint 22 includes conventional removable syringe needle receiver or mount like that found on conventional syringes to removably receive syringe needles and indicated generally at 50, to releasably engage the enlarged blunt mounting end 20*b* of needle 20. In particular, sliding joint 22 is shown with a Luer lock type removable needle receiver or mount 50 having a slip type central spout 50*a* with tapered outer side wall and a surrounding concentric locking collar 50*b* having internal threads 51, which threadingly engage the outwardly flared flange 21*b* at the blunt mounting end 20*b* of the needle 20. Alternatively, the collar 50*b* can be eliminated to define a Luer slip type needle receiver where spout 50*a* is tapered to frictionally engage the tapered inner bore 21*a* of the mating member 21 as the sole needle mount. Also the needle mount of the sliding joint 22 can be molded with one or more integral clip member(s) (not depicted) to snap over the radial flange 21*a*. In the alternative, a bayonet releasable fitting or any other conventional releasable syringe needle receiver can be duplicated on end 22*a* to releasably engage a matingly configured syringe needle. Finally, a syringe needle can be non-removably joined to the sliding joint 22 by being molded into the sliding joint 22 or heat or sonic or solvent welded to a suitable receiver structure on or in the sliding joint, depending upon the material of the sliding joint and construction of the needle. The needle should have an enlarged blunt end 20*b* which will prevent the needle from slipping through or past the sliding joint 22 no matter how hard the sliding joint 22 is pressed against the needle 20 in using device 10.

The second axial end 22*b* of the sliding joint 22 is open and has an inner chamber 54 exposed at the second end 18*b* of the connector 18 (see FIGS. 1-3, 9, 11 and 12) and the device 10. The inner chamber 54 is configured to releasably receive at least the needle mount or receiver 30 of the barrel 27 of the syringe 24 and to also form a leak resistant fluid coupling with the needle mount 30 such that the sliding joint 22 forms a leak resistant fluid connection between the needle 20 and the syringe 24, when all three are assembled as shown in FIGS. 4-6. Specifically, the inner chamber 54 is provided with a needle receiver coupling in the form of a central tubular projection 55 having a generally cylindrical outer sidewall and a generally inwardly tapering inner sidewall designed to extend between and releasably engage the central spout portion 30*a* and surrounding internally threaded collar 30*b* (see FIGS. 5-6) of a conventional Luer type needle receiver 30 at the distal end 32 of the syringe 24 (see FIG. 3). Passageway 56 extends through projection 55 and spout 50*a*. Still referring to FIG. 9, the chamber 54 preferably includes a plurality of circumferentially and radially inwardly projecting ribs 58, which are preferably circumferentially aligned proximal the open end of chamber 54 to support and preferably lightly frictionally grip the barrel 27 of syringe 24.

Referring to FIGS. 9-12, the sliding joint 22 further includes at least two rotational stop members on its outer circumferential surface preferably in the form of first and second spaced apart circumferentially extending radially outwardly projecting shoulders or ribs 61 and 62. Shoulders 61 and 62 each preferably includes a generally sloping surface 61*a*, 62*a* facing passageway 66 and first end 22*a* and a generally radially extending surface 61*b*, 62*b* facing the second end 22*b* of the sliding joint 22 to non-releasably yet slidably retain sliding joint 22 in the second cavity. The second shoulder 62 extends radially outwardly from the adjoining outer circumferential surface of the sliding joint 22 sufficiently far so that the spring clip members 48 distinctly snap against that adjoining surface of sliding joint 22 when they are released after the shoulder 62 cams under and past the members 48. The sliding joint 22 further preferably includes a plurality of circumferentially spaced, axially and radially outwardly projecting protrusions or nibs 63*a*, which are located most proximal to end 22*a* and a plurality 63*b* located most proximal end 22*b*. The sliding joint 22 is supported for sliding movement and centered in the second cavity 46 (FIG. 7) on the radial outermost surfaces of the nibs 63*a*, 63*b*, which minimize the contact area between the sliding joint 22 and the connector 18. Finally, the sliding joint 22 includes at least one and preferably a pair of circumferentially extending ramps 66, 67 projecting radially outwardly and extend circumferentially over arcs of about ninety degrees. Each ramp 66, 67 terminates at its distal radial end with a radially and axially extending sidewall 66*a*, 67*a* (FIG. 12), respectively, which acts as a circumferential stop to engage one of the longitudinal sides of a proximal spring clip member 48 when the syringe 24 is unscrewed from the sliding joint 22 (FIG. 3).

The first open end 18*a* of the connector 18 is configured to be secured over the top of the vial 12 and its stopper 14 by being defined by a transverse end wall 41 of the tubular connector 18, which extends generally radially outwardly, relative to the adjoining portion of the connector 18 defining passageway 66, and a sidewall 34, which extends generally axially from the end wall 41 to form the generally cylindrical first cavity 36. In FIG. 5, first cavity 36 includes an inner cavity portion indicated generally at 36*a*, which snuggly receives the flange 13, stopper 14 and seal 16 of vial 12, and a outer cavity portion 36*b* which has a larger diameter to more easily receive the vial 12 and guide it to the inner portion 36*a*. In FIGS. 1-3 and 7, generally U-shaped slots 35 break the sidewall 34 of the connector 18 defining the first cavity 36 into one or more individual spring clip members or "fingers" 38, which are integral with the connector 18. In FIG. 7, the distal ends of the clip members 38 curve generally radially inwardly and then outwardly to define a necked region 39 of the member 38 and a flared inner surface 40 at the extreme distal end of member 38, which allows the vial 12 with stopper 14 to be inserted into the first cavity 36 at the first end 18*a* of the connector 18 and, more particularly, into the inner portion 36*a* of cavity 36, by spreading the fingers 38 with the top of the vial 12 to expand a necked region 39. The spring clip fingers 38 bias the stopper 14 of the vial 12 against the interior transverse wall 41 of the connector 18, which defines the inner extent of the first cavity 36. An annular projection 42 extends axially outwardly from the interior transverse wall 41 of the connector 18 toward the vial 12 and provides a tight seal between the connector 18 and a portion of the stopper 14 surrounding a needle injection site at the center of the stopper 14. Preferably, diametrically opposed bosses 37 project inwardly from the sidewall 34 in the outer cavity portion 36*a* between fingers 38 to limit the degree the vial 12 can be twisted side to side in cavity 36. While individual fingers 38 are formed within the sidewall of the connector 18, it will be appreciated that the fingers 38 might be extended to the distal end of the sidewall and cavity 36. However, the cantilever fingers 38 disclosed, which are surrounded on all sides by non-movable portions of the connector 18, make removal of the vial 12 from the connector 18 difficult and make accidental removal nearly impossible.

In FIG. 7, the second cavity 46 and passageway 66 take up the remainder of the length of the connector 18. A first end 66*a* of the passageway 66, which is most proximal the first end 18*a*, extends to the interior transverse wall 41. The passageway 66 includes a central opening 43 through wall 41. The opening 43 is effectively sealed by the stopper 14 of a vial 12 secured in the cavity 36. A second end 66*b* of the passageway 66 extends to a circumferential shoulder 28 of the connector 18 which defines an innermost extent of the second cavity 46. The second end 66*b* of the passageway 66 is preferably sealed by the combination of the sliding joint 22 and the syringe 24. The inner surface 69 of the passageway 66 is preferably inwardly tapered as the surface moves axially from the second end 18*b* toward the first end 18*a* of the connector 18 to provide a shield for the distal (pointed) end 20*b* of the needle 20 when the needle 20 is displaced within the connector 18. Preferably, connector 18 can include a plurality of ribs 70 which project radially outwardly from a conical sidewall 71 defining passageway 66 and extend axially between end wall 41 and shoulder 28 to strengthen the connector 18 between the cavities 36, 46.

The second open ended cavity 46 is defined by a second, generally cylindrically shaped sidewall 44 of connector 18, which extends axially away from shoulder 28 to the second end 18*b*. Preferably, one or more generally U-shaped slots 47 in the sidewall 44 separate one or more of the spring clip members or fingers 48 from the remainder of the connector 18. Preferably, fingers 48 are integrally molded as part of the connector 18 and slope radially inwardly into the cavity 46 as the fingers 48 extend axially from their base connection with the remainder of the connector 18 towards the first end 18*a* of the connector. The shoulders 61, 62 are sized and spaced such that the sliding joint 22 is inserted until the first shoulder 61 cams completely under and past the fingers 48 (FIGS. 4 and 5). The sliding joint 22 is then captured by interference between fingers 48 and radial surface 61*b* of shoulder 61. This is the first stop position shown in FIG. 5. The sliding joint 22 and needle 20 can be slid further into the connector 18 and back and forth to the first stop position until the second shoulder 62 cams under and past fingers 48 (FIG. 6). This is the second stop position. Preferably at the second stop position, the inner end 22*a* of sliding joint 22 abuts against shoulder 28. While it is preferable that the sliding joint 22 has a generally cylindrical shape, those of ordinary skill in the art will appreciate from this disclosure that the sliding joint 22 can have a circumferential outer surface with any shape which is complementary to the inner surface of the second cavity 46 within which the sliding joint 22 moves.

The syringe safety device 10 preferably operates as follows. The connector 18 is preferably preassembled with a filled syringe 24 attached to the needle receiver coupling/projection 55 of the sliding joint 22, the needle 20 attached to the receiver 50 of the sliding joint 22 (FIG. 1) and the sliding joint 22 and needle 20 inserted into the tubular connector 18 (FIG. 2) sufficiently for fingers 48 to engage rib 61. The sliding joint 22 is preferably provided in the second end 18*b* of the connector 18 and non-releasably retained by engagement of the fingers 48 of the connector 18 with rib 61. The device 10 and attached syringe 24 are preferably provided joined together in suitable sealed, sterile packaging such as a sterile blister pack. After the device 10 and syringe 24 are removed from their packaging and/or any other cover(s) removed, the first end 18*a* of the connector 18 is snapped over the flange end 14 top of a stopper sealed vial 12 as shown in FIGS. 3-6. Again, the spring clip members 38 are designed to produce a snap sound (against the side of the vial) as the members 38 cam over the flange end 14 of the vial 12 and drop behind the flange 14 to lock the vial 12 in the device 10. The syringe 24 and the sliding joint 22 are pushed into the tubular connector 18 until the other spring clip members 48 snap over the second circumferential rib 62. A user can grip finger grips 64*a*, 64*b* to displace the sliding joint 22 generally radially inwardly to cause the needle 20 on the sliding joint 22 to perforate the stopper 14. It may be desirable to inwardly taper the sidewall 44 of the second cavity 46 slightly to provide some resistance to the inward movement of the sliding joint 22. As the sliding joint 22 moves inwardly, the pointed tip 20*a* of needle 20 passes through opening 43, annular projection 42 and the stopper 14 and into the vial 12 to place the syringe 24 in fluid communication with the interior of the vial 12 as shown in FIG. 6. By the time the members 48 snap over the second rib 62, the pointed end 20*a* of needle 20 has penetrated the stopper 14 of vial 12. Hearing both snaps tells the user that the vial 12 has been successfully engaged and that the sliding joint 22 has moved sufficiently so that the stopper 14 has been penetrated by the needle 20.

Then, the user depresses the plunger rod 26 to empty any contents of the syringe barrel 27 into the vial 12. The vial 12 and the syringe safety device 10 are then shaken to mix the fluid from the syringe 24 with the contents of the vial 12. After the mixture is ready for use, the plunger rod 26 is partially withdrawn from the barrel 27 of the syringe 24 to cause the mixture in the vial 12 to be drawn into the syringe 24. After a desired amount of the mixture is drawn into the syringe 24, the syringe 24 can be detached from the syringe safety device 10 (FIG. 3) without removing the needle 20 from the syringe safety device 10. The syringe 24 can then be attached via the needle receiver/mount 30 to a catheter or other tube or an intravenous bottle or bag or the like with a matingly configured conventional removable syringe connection (not depicted).

Alternatively, the device 10 can be packaged by itself or with an attached vial 12. If by itself, The axial ends 12*a*, 12*b* of the device 10 can be sealed before use by suitable means, such as peel away foils 72*a*, 72*b* (phantom in FIG. 2) or other suitable, removable cover(s), and/or supplied in a sealed package such as a blister pack for sterility. If with a vial 12, the device 10 and vial 12 can be combined in a suitable sealed sterile packaging. In use, the device 10 is removed from the packaging and/or any individual seals removed and the vial 12 attached if not already attached to device 10 in the package. The distal end 32 of syringe 24 is then inserted into the sliding joint 22 (FIG. 2) sufficiently into the chamber 54 and, if appropriate, rotated to create a tight connection between the needle receiver or mount 30 of the syringe 24 and the needle receiver coupling 55 of the sliding joint 22 as shown in FIG. 4. The exposed end of the sliding joint 22 may have to be gripped to do this or one or more ramps could be provided in the area between ribs 61, 62 along the outer surface of the sliding joint 22, to engage the sides of fingers 48 and stop the sliding joint 22 from rotating in a clockwise direction in that area to permit the syringe 24 to be screwed onto an appropriately threaded receiver coupling/projection 55. After the syringe 24 is joined, the syringe 24 and sliding joint 22 are pushed deeper into the connector 18 as described above until the second rib 62 cams under and past the free ends of the fingers 48. The rest of the use of the combination is as described above.

While the preferred embodiment of the syringe safety device 10 uses a connector 18 that is a separate component from the vial 12 and syringe 24, those of ordinary skill in the art will appreciate from this disclosure, that the connector 18 can be manufactured as an integral part of the vial 12 or syringe 24 (or both) without departing from the scope of the present invention. Also, the connector can be supplied coupled with a vial 14 with medication or with a syringe 24 (with or without fluid) or with both a vial and syringe in sterile sealed packaging. Referring to FIGS. 1, 2 and 7, a second sterile sealed package 94 enclosing the syringe safety device 10 and syringe 24, a first sterile sealed package 92 enclosing the syringe safety device 10 and vial 12 and a third sterile sealed package 96 enclosing the syringe safety device 10, syringe 24 and vial 12 are indicated diagrammatically, in phantom in FIG. 2 at 92, 94 and 96, respectively. The syringe 24 without needle may be a liquid filled, self-sealing syringe like a Becton-Dickenson ReadyFill™ or other self-sealed or otherwise sealed syringe or may be empty. Also, it will be appreciated that a septum, which could be penetrated by needle 20, can be positioned at the transverse wall 41 to seal the needle 20 in the connector 18, if desired. Such septum could itself be provided with an annular projection like 42. U.S. Patent Application No. 60/246,635 filed Nov. 8, 2000, is incorporated by reference herein in its entirety.

It is recognized by those of ordinary skilled in the art, that changes could be made to the embodiment of the invention without departing from the broad inventive concept thereof. It is understood, therefore, that this invention is not limited to the particular embodiment disclosed, but it is intended to cover all modifications which are within the spirit and scope of the present invention as defined by the appended claims.

We claim:

1. A syringe safety device configured to form a fluid coupling between a sealed vial and a syringe, the syringe safety device comprising:

a tubular connector having opposing first and second open axial ends, the first open axial end engaging an end of the sealed vial; and a sliding joint received in the second open axial end of the tubular connector, the sliding joint having opposing first and second open axial ends and a passageway between the first and second open axial ends, the first open axial end releasably mating with an enlarged, blunt mounting end of a syringe needle, the second axial end of the sliding joint further releasably engaging at least a releasable needle receiver on a distal end of the syringe without a needle, at least part of the passageway extending between the needle receiver and the mounting end of the syringe needle when the syringe, syringe needle and sliding joint are assembled, the syringe being releasably removable from the sliding joint after fluid coupling with the vial through the passageway of the sliding joint without removal of the sliding joint from the tubular connector and without removal of the syringe needle.

2. The syringe safety device according to claim 1 further comprising a syringe needle with one pointed end and one enlarged, blunt removable mounting end, the needle being non-releasably captured in the tubular connector with the sliding joint.

3. The syringe safety device according to claim 1 wherein the first axial end of the sliding joint includes a needle receiver that releasably engages the blunt mounting end of the enclosed needle.

4. The syringe safety device according to claim 1 wherein the second axial end of the sliding joint is open and has an inner chamber exposed at the second end of the tubular connector, the inner chamber releasably receiving at least a needle mount provided on the distal end of the syringe to removably mount a needle to the distal end of the syringe.

5. The syringe safety device according to claim 1 wherein the sliding joint has a needle receiver at the first axial end that engages with the enlarged blunt end of the needle and a needle receiver engaging structure at the second axial end that releasably receives the needle receiver of the syringe.

6. A syringe safety device configured to form a fluid coupling between a sealed vial and a syringe, the syringe safety device comprising:

a tubular connector having opposing first and second open axial ends, the first open axial end engaging an end of the sealed vial;

a needle having a mating member, the mating member having at least one radially outwardly extending proximal flange; and a sliding joint received in the second open axial end of the tubular connector, the sliding joint having opposing first and second open axial ends and a passageway between the first and second open axial ends, the first open axial end having a needle receiver releasably engaging with the mating member of the needle, the second axial end of the sliding joint having a needle receiver engaging structure releasably receiving a Luer type needle receiver on a distal end of a barrel of the syringe, whereby the sliding joint can be releasably engaged between the needle and a syringe within the tubular connector and the syringe can be directly releasably engageable with the mating member of the needle outside of the tubular connector, the syringe being releasably removable from the sliding joint after fluid coupling with the vial through the passageway of the sliding joint without removal of the sliding joint from the tubular connector and without removal of the needle.

7. The syringe safety device according to claim 1 in combination with the sealed vial.

8. The combination in accordance with claim 7 wherein the syringe safety device and the vial are packaged together in sealed, sterile packaging.

9. The syringe safety device according to claim 1 in combination with the syringe without needle.

10. The combination according to claim 9 wherein the syringe safety device and the syringe are packaged together in sealed, sterile packaging.

11. The combination according to claim 10 further comprising the sealed vial packaged together with the syringe safety device and the syringe in the sealed, sterile packaging.

12. The syringe safety device according to claim 1 wherein the tubular connector has an open ended cavity at the first open axial end receives a flange end of a vial with stopper and wherein the tubular connector has at least one spring clip member extending into the cavity and snaps against a vial inserted into the first cavity after the flange end of the inserted vial has cammed under and past the at least one spring clip member.

13. The syringe safety device according to claim 11 wherein the at least one spring clip member non-releasably engages the flange of a vial cammed under and past the at least one spring clip member.

14. A syringe safety device configured to form a fluid coupling between a sealed vial and a syringe, the syringe safety device comprising:

a tubular connector having opposing first and second open axial ends, the first open axial end engaging an end of the sealed vial;

a needle having a mating member releasably mountable to a distal end of the syringe outside of the tubular connector; and a sliding joint received in the second open axial end of the tubular connector, the sliding joint having opposing first and second open axial ends and a fluid passageway between the first and second open axial ends, the first open axial end having a needle receiver releasably and selectably engaging with the mating member of the needle, the second axial end of the sliding joint having an engaging structure releasably receiving the distal end the syringe, whereby the sliding joint can be releasably engaged between the mating member of the needle and the distal end of the syringe within the tubular connector to form a fluid connection between the sealed vial and the syringe, the syringe being releasably removable from the sliding joint after fluid coupling with the vial through the fluid passageway of the sliding joint without removal of the sliding joint from the tubular connector and without removing the needle from the tubular connector and sliding joint.

* * * * *